(12) United States Patent
Karlsson et al.

(10) Patent No.: US 11,690,956 B2
(45) Date of Patent: Jul. 4, 2023

(54) SUB-ASSEMBLY OF A MEDICAMENT DELIVERY DEVICE AND A MEDICAMENT DELIVERY DEVICE

(71) Applicant: CAREBAY EUROPE LTD, Sliema (MT)

(72) Inventors: Sebastian Karlsson, Stigtomta (SE); Anders Boström, Solna (SE); Brian Maxfield, Boca Raton, FL (US); Mattias Daniel, Täby (SE)

(73) Assignee: SHL MEDICAL AG, Zug (CH)

( * ) Notice: Subject to any disclaimer, the term of this patent is extended or adjusted under 35 U.S.C. 154(b) by 550 days.

(21) Appl. No.: 15/566,316

(22) PCT Filed: Apr. 1, 2016

(86) PCT No.: PCT/EP2016/057243
§ 371 (c)(1),
(2) Date: Oct. 13, 2017

(87) PCT Pub. No.: WO2016/169748
PCT Pub. Date: Oct. 27, 2016

(65) Prior Publication Data
US 2018/0104414 A1 Apr. 19, 2018

(30) Foreign Application Priority Data
Apr. 24, 2015 (SE) .................................. 1550494-7

(51) Int. Cl.
*A61M 5/20* (2006.01)

(52) U.S. Cl.
CPC ... *A61M 5/2033* (2013.01); *A61M 2005/2013* (2013.01); *A61M 2207/00* (2013.01); *A61M 2207/10* (2013.01)

(58) Field of Classification Search
CPC ........ A61M 5/315; A61M 5/20; A61M 5/142; A61M 5/46; A61M 5/2033;
(Continued)

(56) References Cited

U.S. PATENT DOCUMENTS 5,300,030 A * 4/1994 Crossman .......... A61M 5/31511
                                                           604/157
6,544,234 B1 * 4/2003 Gabriel ............... A61M 5/3271
                                                           604/218
(Continued)

FOREIGN PATENT DOCUMENTS

CN       1738657 A     2/2006
CN     101583391 A    11/2009
(Continued)

OTHER PUBLICATIONS

International Search Report and Written Opinion for Int. App. No. PCT/EP2016/057243, dated Jul. 4, 2016.

*Primary Examiner* — Bradley J Osinski
*Assistant Examiner* — William R Frehe
(74) *Attorney, Agent, or Firm* — McDonnell Boehnen Hulbert & Berghoff LLP

(57) ABSTRACT

A sub-assembly of a medicament delivery device is presented, where the sub-assembly includes a plunger rod that is biased, a main body arranged on the plunger rod, and a coupling member movable relative to the main body, where the main body includes a first locking element, the coupling member includes a second locking element, and where the first locking element and the second locking element are configured to be releasably engaged with each other such that the coupling member is prevented from moving relative to the main body.

14 Claims, 14 Drawing Sheets

(58) Field of Classification Search
CPC .......... A61M 5/31501; A61M 5/31571; A61M 2005/2073; A61M 5/3135; A61M 2005/31508

See application file for complete search history.

(56) References Cited

U.S. PATENT DOCUMENTS

| | | | |
|---|---|---|---|
| 7,699,816 B2* | 4/2010 | Kirchhofer | A61M 5/3158 604/218 |
| 7,887,506 B1* | 2/2011 | Smolyarov | A61M 5/20 604/68 |
| 8,591,463 B1* | 11/2013 | Cowe | A61M 5/20 604/117 |
| 8,827,956 B2 | 9/2014 | Banik et al. | |
| 9,789,255 B2* | 10/2017 | Brereton | A61M 5/2033 |
| 10,376,642 B2* | 8/2019 | Brereton | A61M 5/2033 |
| 2009/0281496 A1 | 11/2009 | Matusch | |
| 2010/0049125 A1* | 2/2010 | James | A61M 5/2033 604/110 |
| 2010/0160894 A1* | 6/2010 | Julian | A61M 5/2033 604/506 |
| 2011/0251587 A1* | 10/2011 | Banik | A61M 5/3287 604/117 |
| 2013/0035642 A1* | 2/2013 | Daniel | A61M 5/2033 604/189 |
| 2013/0096591 A1 | 4/2013 | Hart et al. | |
| 2013/0317427 A1* | 11/2013 | Brereton | A61M 5/2033 604/111 |
| 2014/0207106 A1* | 7/2014 | Bechmann | A61M 5/2033 604/506 |
| 2016/0008540 A1* | 1/2016 | Fourt | A61M 5/31581 604/223 |
| 2016/0045669 A1* | 2/2016 | Bayer | A61M 5/20 604/207 |
| 2016/0193413 A1* | 7/2016 | Gabrielsson | A61M 5/3204 604/135 |
| 2016/0303327 A1 | 10/2016 | Moren | |
| 2016/0310160 A1 | 10/2016 | Hart et al. | |
| 2017/0014574 A1* | 1/2017 | Ogawa | A61M 5/3137 |
| 2017/0290981 A1* | 10/2017 | Hoeholt | A61M 5/315 |
| 2018/0001026 A1* | 1/2018 | Brereton | A61M 5/2033 |
| 2019/0231380 A1 | 8/2019 | Hart et al. | |

FOREIGN PATENT DOCUMENTS

| | | |
|---|---|---|
| CN | 102137691 A | 7/2011 |
| CN | 103476444 A | 12/2013 |
| JP | 2013-526904 A | 6/2013 |
| TW | 566299 U | 12/2003 |
| TW | 201505681 A | 2/2015 |
| WO | 2010/108116 A1 | 9/2010 |
| WO | 2011/123024 A1 | 10/2011 |
| WO | 2011/153529 A2 | 12/2011 |
| WO | 2012/143437 A1 | 10/2012 |
| WO | 2013/016832 A1 | 2/2013 |
| WO | 2014/154491 A1 | 10/2014 |
| WO | 2015/028394 A1 | 3/2015 |

* cited by examiner

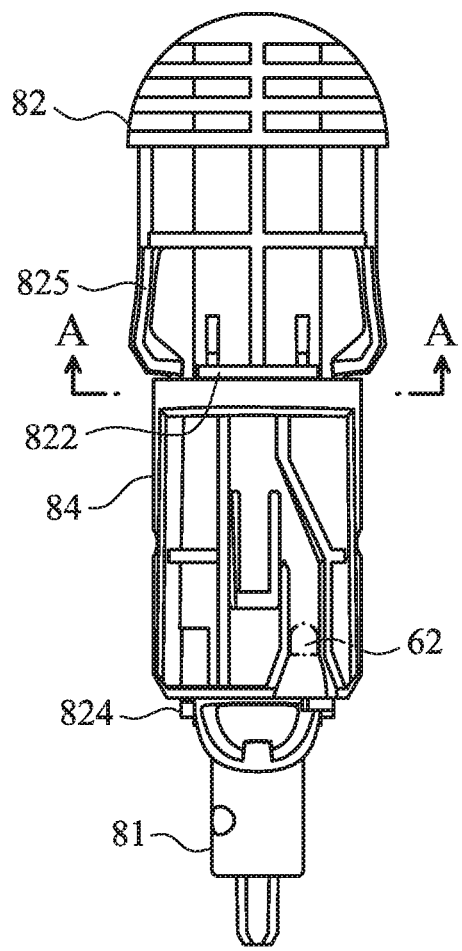 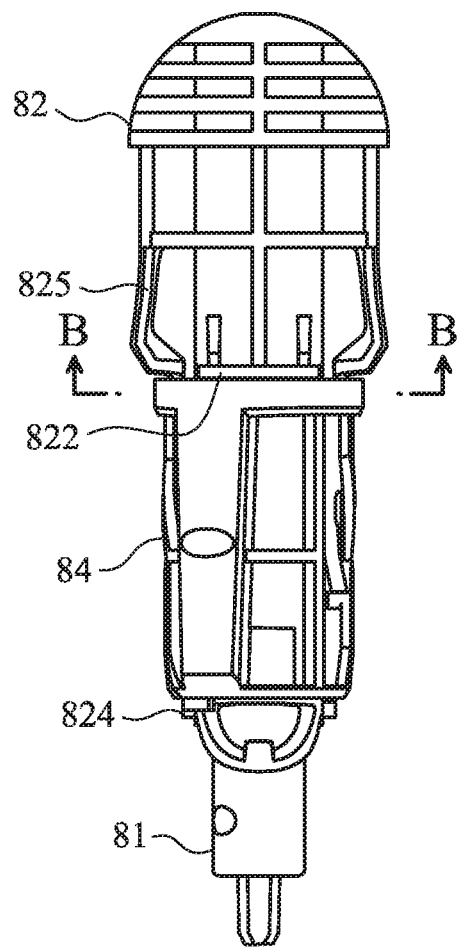
Fig. 5A  Fig. 6A
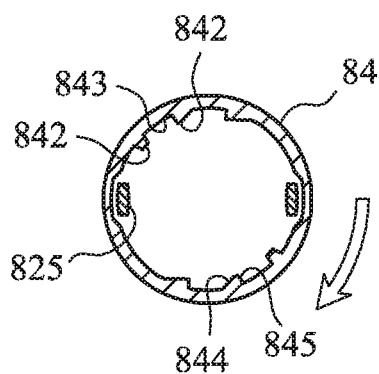 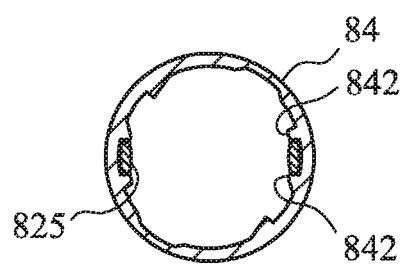
Fig. 5B  Fig. 6B

SUB-ASSEMBLY OF A MEDICAMENT DELIVERY DEVICE AND A MEDICAMENT DELIVERY DEVICE

CROSS REFERENCE TO RELATED APPLICATIONS

The present application is a U.S. National Phase application pursuant to 35 U.S.C. § 371 of International Application No. PCT/EP2016/057243 filed Apr. 1, 2016, which claims priority to Swedish Patent Application No. 1550494-7 filed Apr. 24, 2015. The entire disclosure contents of these applications are herewith incorporated by reference into the present application.

TECHNICAL FIELD

The present invention generally relates to a sub-assembly of a medicament delivery device, and more particularly to a sub-assembly comprising a transportation locking mechanism.

BACKGROUND

FIG. 1 shows a conventional medicament delivery apparatus 1 disclosed in WO 2011/123024 A1, which will be incorporated into the present invention as a reference. The conventional medicament delivery apparatus 1 generally comprises a second sub-assembly 2, an inner sub-assembly 3 and a first sub-assembly 4. The inner sub-assembly 3 may include a medicament container 31 and a piston 32 which is slidably received in the medicament container 31. The first sub-assembly 4 may include a plunger rod 41, a tubular extension part 42 which slidably receives the plunger rod 41, a spring which is accommodated between the plunger rod 41 and the extension part 42, and an operation member 44 which is arranged on the extension part 42.

When the conventional medicament delivery apparatus 1 is in an initial state, the operation member 44 is arranged on the extension part 42 at a specific angle and the plunger rod 41 is held by the extension part 42. In this state, a drive spring is held pre-tensioned to urge the plunger rod 41 proximally. In a subsequent injection state, the operation member 44 is rotated by the front sub-assembly 2 to another specific angle relative to the extension part 42, the operation member 44 then allows the extension part 42 to release the plunger rod 41 so that the spring can push the plunger rod 41 out of the extension part 42. The plunger rod 41 subsequently drives the piston 32 proximally in the medicament container 31 to expel medicament out of the container 31.

However, elements of the conventional medicament delivery apparatus 1 may be manufactured and then assembled into the three sub-assemblies 2, 3, and 4 in a factory. The three sub-assemblies 2, 3, and 4 may then be transported or shipped to another factory for sterilization and final assembly. During the transportation or shipment, the operation member 44 of the first sub-assembly 4 may accidentally rotate relative to the extension part 42. Such a rotation of the operation member 44 will cause the extension part 42 to release the plunger rod 41 prematurely.

Besides, connection between the second sub-assembly 2 and the first sub-assembly 4 in the final assembly of the conventional device may be insecure. Hence, the two sub-assemblies 2 and 4 may accidentally separate from each other.

SUMMARY

Accordingly, the present invention relates to a sub-assembly of a medicament delivery device having locking elements that are substantially intended to eliminate one or more of the problems encountered in the prior art.

One object of the present invention is to provide a sub-assembly of a medicament delivery device with locking elements which can prevent unexpected rotation of a coupling member relative to a main body, such as during transportation of the sub-assembly.

Another object of the present invention is to provide a sub-assembly of a medicament delivery device with locking elements which can prevent a plunger rod from being released out of a main body prematurely.

Another object of the present invention is to provide a sub-assembly of a medicament delivery device with locking elements which can improve the mechanical connection between a proximal housing and a main body.

Yet another object of the present invention is to provide a easy and intuitive mechanism for releasing the transportation lock when medicament delivery device is assembled.

These objects are achieved by a medicament delivery device with locking elements as defined by the claims as well as a sub-assembly of the medicament delivery device. The dependent claims define preferred or advantageous embodiments of the medicament delivery device and of the sub-assembly.

Additional features and advantages of the present invention will be set forth in the following description, claims and drawings.

To achieve these and other advantages and according to the purpose of the present invention, as embodied and broadly described, a sub-assembly of a medicament delivery device comprises: a plunger rod which is biased; a main body arranged on the plunger rod, which main body comprises a first locking element; a coupling member being movable relative to the main body and comprising a second locking element. The first locking element and the second locking element are configured to be in a releasable engagement with each other such that the coupling member is prevented from moving relative to the main body.

Moreover, the first locking element extends in an axial direction of the main body, then extends radially outwards in an arch, and then extends radially inwards so that a free end of the first locking element is engaged with the second locking element to prevent the coupling member from rotating relative to the main body.

It is another preferred feature that a distance between the arch and a central axis of the main body is larger than a distance between the central axis and other portions of the first locking element, and also larger than an outer radius of the coupling member.

Additionally, the coupling member includes a bore at a distal end thereof and two protrusions which extend from an inner surface of the bore and delimit the second locking element.

Furthermore, the main body includes a rib which divides the main body into a proximal section and a distal section, the coupling member is arranged on the proximal section, and a fixed end of the first locking element is arranged on the distal section.

It is preferred that the main body includes a wall at the distal section thereof to enforce the first locking element.

It is preferred that one of the two protrusions has a ramp-shaped first surface which extends inwards from the inner surface of the bore for bending the first locking element and a wall-shaped second surface which extends orthogonally from the inner surface of the bore for fixing the first locking element relative to the coupling member.

In another embodiment it is preferred that the coupling member includes a closed loop at an outer proximal end thereof and a protrusion situated in the closed loop, the protrusion and a profile of the closed loop delimit the second locking element for preventing the coupling member from rotating relative to the main body.

It is preferred that the main body further comprises a biasing member guide which is fixed to the coupling member and a distal cap relative to which the coupling member is rotatable.

It is preferred that the first locking element is a radially flexible tab and that the second locking element is a recess.

It is preferred that the first locking element extends from the distal cap, the first locking element includes a latch and that the coupling member comprises a circumferential ledge at the distal section thereof. The latch is engaged with the ledge to prevent the coupling member from detaching from the distal cap in the proximal direction.

It is preferred that the first locking element extends radially inwards at a free end. The second locking element is arranged on an inner surface of the coupling member, and the first locking element is engaged with the second locking element to prevent the coupling member from rotation and axial movement relative to the main body.

It is preferred that the main body includes a rib which divides the main body into a proximal section and a distal section, the coupling member is movably arranged on the proximal section.

It is preferred that the first locking element is a radial projection and the second locking element is a recess.

It is preferred that the sub-assembly further comprises a biasing member which biases the plunger rod.

Another aspect of this invention directs to a medicament delivery device with locking elements. The medicament delivery device comprises: a second sub-assembly including a proximal housing; and a first sub-assembly described above.

Moreover, the housing is configured to interact with the first locking element such that the first locking element and the second locking element are configured to be released from each other upon assembly of the first sub-assembly with the second sub-assembly. Also, a distance between the first locking element and a central axis of the main body is larger than an inner radius of the proximal housing before the main body is assembled, and the first locking element is bent by the proximal housing to release out of the second locking element when the first sub-assembly is mounted to the second sub-assembly.

It is to be understood that both the foregoing general description and the following detailed description are exemplary and explanatory and are intended to provide a further non-limiting explanation of the present invention as claimed.

BRIEF DESCRIPTION OF THE FIGURES

The accompanying drawings, which are included to provide a further understanding of the present invention and constitute a portion of the specification, illustrate embodiments of the present invention, and together with the description serve to explain the principle of the present invention.

FIG. 5A is an assembled plain view of the first sub-assembly of the first embodiment illustrating a state that a coupling member is not locked by a tab;

FIG. 5B is a sectional view of FIG. 5A taken along a line A-A;

FIG. 6A is an assembled plain view of the first sub-assembly of the first embodiment illustrating a state that a coupling member is locked by a tab;

FIG. 6B is a sectional view of FIG. 6A taken along a line B-B;

DETAILED DESCRIPTION

In the present invention, the term "proximal part/end" refers to the part/end of the medicament delivery device, or the parts/ends of the members thereof, which is/are located closest to the medicament delivery site of a patient. Correspondingly, the term "distal part/end" refers to the part/end of the medicament delivery device, or the parts/ends of the members thereof, which is/are located farthest away from the medicament delivery site of the patient.

First Embodiment

Figure 1:
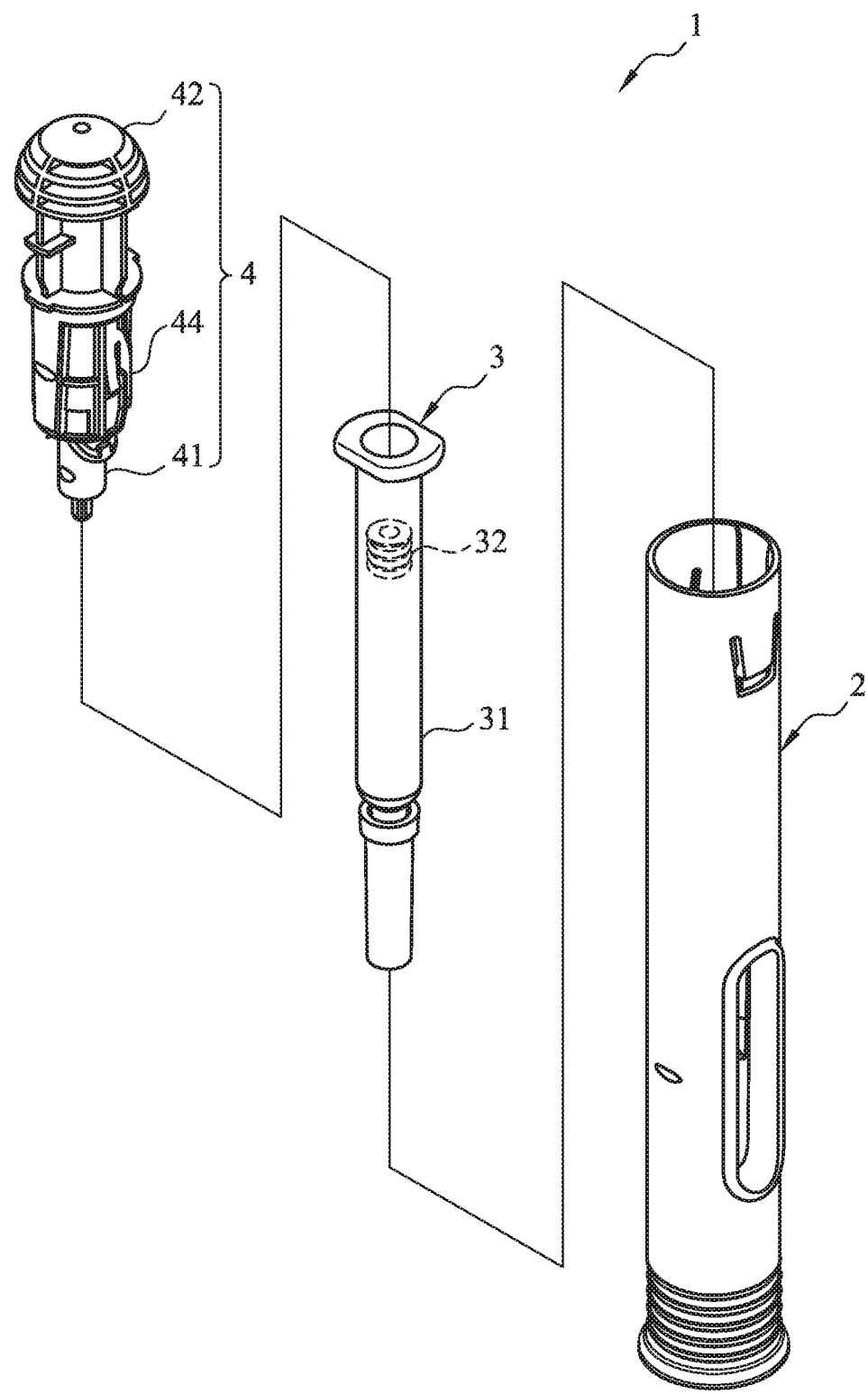
FIG. 1 is an exploded perspective view of a conventional medicament delivery apparatus.
Figure 2:
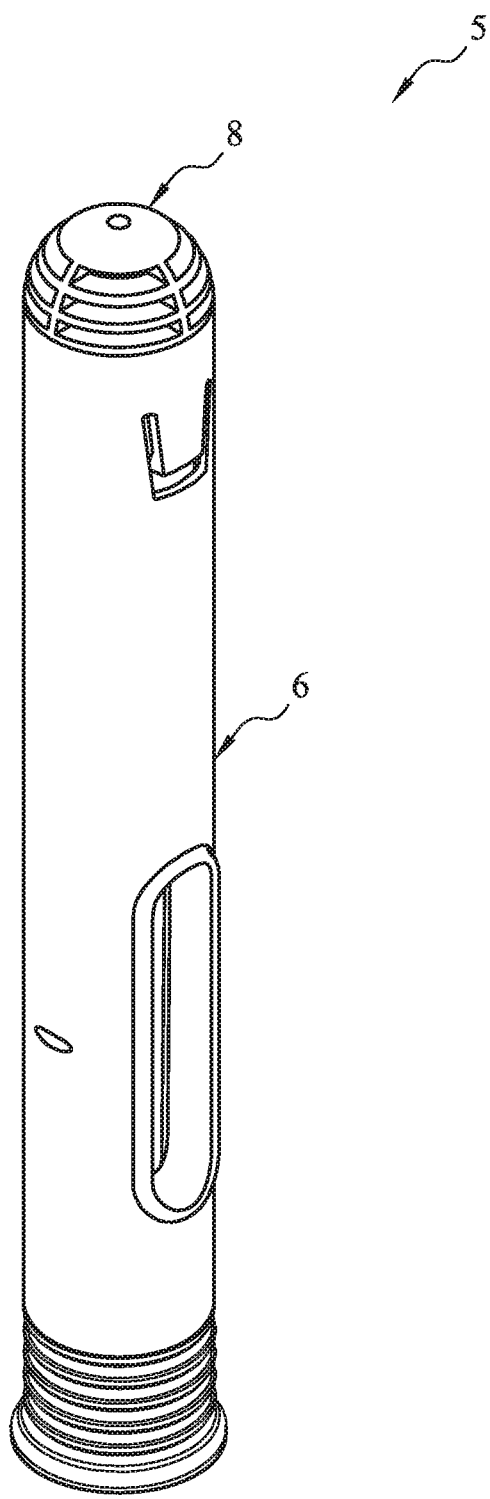
FIG. 2 is an assembled perspective view of the first embodiment of the medicament delivery apparatus according to the present invention.
Figure 3:
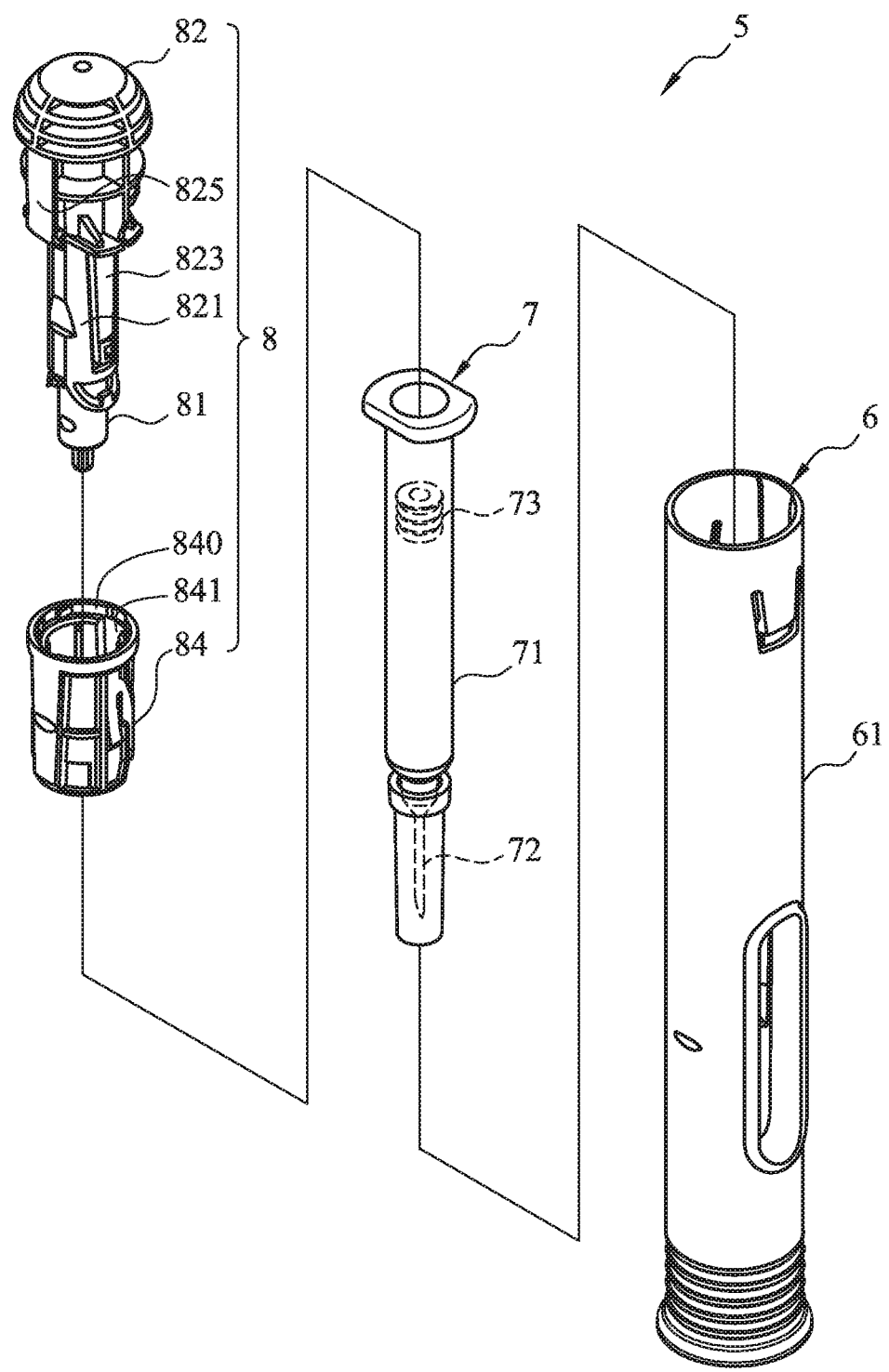
FIG. 3 is an exploded perspective view of the first embodiment illustrating three sub-assemblies.
Figure 4:
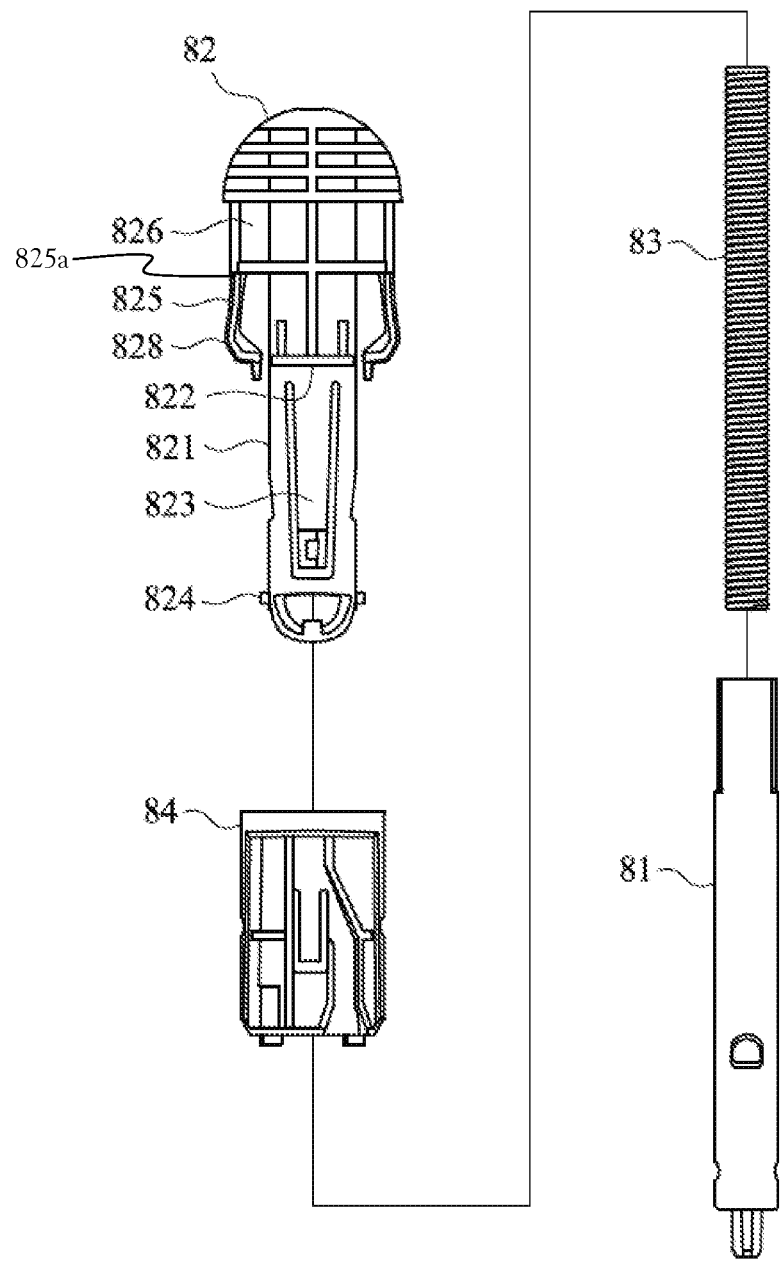
FIG. 4 is an exploded plain view of the first sub-assembly of the first embodiment.
Figure 7:
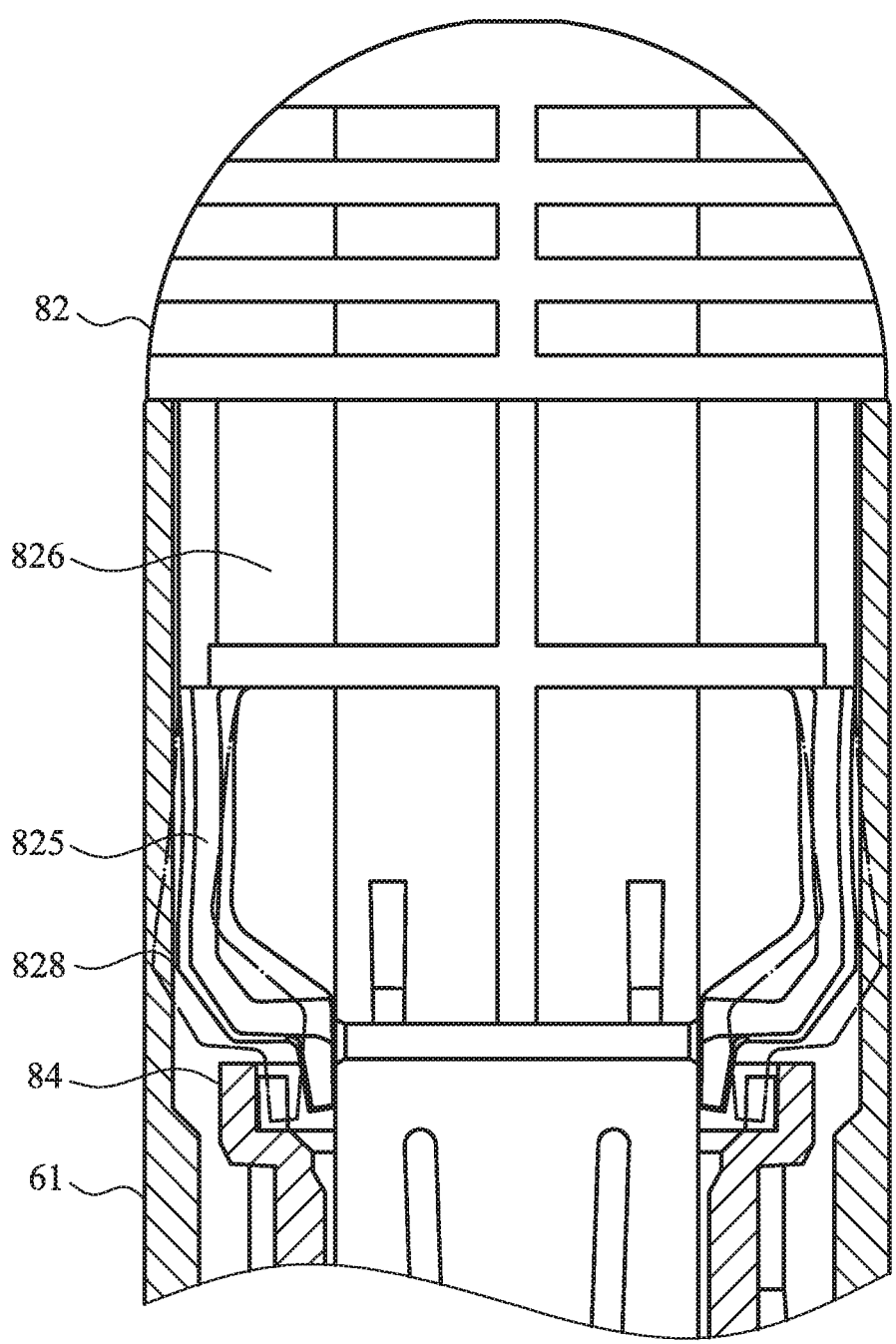
FIG. 7 is a partially enlarged sectional view illustrating different positions of a tab in a final assembly of the first embodiment.

As shown in FIGS. 2, 3 and 4, a medicament delivery device 5 with locking elements is generally cylindrical and comprises a second sub-assembly 6, a first sub-assembly 8 and an intermediate sub-assembly 7 which is arranged between the second sub-assembly 6 and the first sub-assembly 8. Compared to the WO 2011-123024A1, the present invention will focus on the first sub-assembly 8 and connection between the first sub-assembly 8 and the second sub-assembly 6.

The second sub-assembly 6 may include a proximal housing 61 which encloses most of the other elements of the second sub-assembly 6, and a protrusion 62 (FIGS. 5A and 13~15) inside the second sub-assembly 6. The intermediate sub-assembly 7 may include a container 71, a cannula 72 connected to a proximal end of the container 71, and a stopper 73 which is slidably received in the container 71. The first sub-assembly 8 may include a plunger rod 81, a main body 82 which slidably receives the plunger rod 81, a biasing member 83 which is accommodated radially between the plunger rod 81 and a guide rod of the main body 82 for biasing the plunger rod 81. A coupling member 84 is movably arranged on the main body 82.

The main body 82 of the first embodiment may comprise a hollow cylinder 821 A rib 822 radially extends from the cylinder 821 and divides the cylinder 821 into a proximal section and a distal section. A radially flexible arm 823 is formed in the proximal section and constitutes a portion of the cylinder 821. The flexible arm is configured to be directly connected to the plunger rod 81 to hold the biased plunger rod until the medicament delivery device is assembled and activated. A projection 824 extends radially from a proximal end of the proximal section. At least one flexible tab 825 longitudinally extends proximally from a fixed end 825a of the distal section. In the first embodiment, the main body 82 has two tabs 825 which are oppositely arranged relative to the longitudinal axis. A longitudinal wall 826 radially extends outwards from the cylinder 821 and abuts a distal portion of the tab 825 to radially support tab 825. A proximal half of the tab 825 may extend radially outwards from the longitudinal axis of the main body 82, and then radially inwards to form an arch 828. Hence, a distance between the arch 828 and the central axis is larger than a distance between other portions of the tab 825 and the central axis, and also larger than an outer radius of the coupling member 84 and an inner radius of the proximal housing 61.

As shown in FIGS. 3 and 5A~6B, the coupling member 84 of the first embodiment may include a central through-hole through the coupling member 84, a bore 840 concentrically formed at a distal end of the coupling member 84 and having an inner diameter larger than that of the through-hole, a longitudinal groove 841 formed in an inner surface of the through-hole, at least two protrusions 842 extending from an inner surface of the bore 840, and a recess 843 formed between two protrusions 842. One of the protrusions 842 may have a ramp-shaped first surface 844 extending inwards from the inner surface of the bore 840 and a second wall-shaped surface 845 extending orthogonally from the inner surface of the bore 840. Another (adjacent) protrusion 842 may have two second surfaces 845 radially extending from the inner surface of the bore 840.

When the coupling member 84 is mounted on the proximal section of the main body 82, the projection 824 of the main body 82 passes along the longitudinal groove 841 of the coupling member 84 and then exits from the proximal end of the coupling member 84. In this state, the free end of the tab 825 of the main body 82 is also received within the bore 840 of the coupling member 84.

Subsequently, the coupling member 84 may be rotated relative to the main body 82. Due to the rotation, the projection 824 of the main body 82 is no longer aligned with the longitudinal groove 841 of the coupling member 84 which prevents the coupling member 84 from detaching from of the main body 82 in the proximal direction. Furthermore, when the coupling member 84 is rotated, the ramp-shaped first surface 844 of the protrusion 842 of the coupling member 84 bends the free end of the tab 825 radially inwards, i.e. towards the longitudinal central axis of the main body 82, whereupon the free end of the tab 825 snaps into the recess 843. The tab 825 thereby recovers outwards and the free end of the tab 825 is confined between two second wall-shaped surfaces 845 of two adjacent protrusions 842. In this state, the coupling member 84 is prevented from rotation relative to the main body 82. In the first embodiment, the tab 825 is a first locking element and the recess 843 is a second locking element. Engagement of the first locking element with the second locking element rotationally locks the coupling member 84 to the main body 82. Since the coupling member 84 is rotationally locked to the main body 82, the flexible arm 823 is confined by the coupling member 84 and the free end of the flexible arm 823 locks the plunger rod 81. Hence, the plunger rod 81 which is biased by the biasing member 83 cannot be released from the main body 82 until it is unlocked by assembly of the first sub-assembly 8 with the second sub-assembly 6.

As shown in FIGS. 3 and 5A~7, after transportation and shipment, the three sub-assemblies 6, 7 and 8 may be assembled to form a final assembly of the medicament delivery device 5. In the final assembly, most of the first sub-assembly 8 is accommodated within the second sub-assembly 6. An inner surface of the proximal housing 61 bends the proximal half of the tab 825 inwards to the extent that the free end of the tab 825 is totally released from confinement of the protrusions 842 so that the coupling member 84 is ready to be rotated by other elements of the medicament delivery device 5.

On the other hand, when the second sub-assembly 6 and the first sub-assembly 8 are assembled, the distal half of the tab 825 resiliently abuts against the inner surface of the proximal housing 61 to make them tightly fitted. In this state, the wall 826 supports the distal half of the tab 825 to reinforce a radial tension force between the tab and the inner surface of the proximal housing 61 to prevent the first sub-assembly 8 from detaching from the second sub-assembly 6.

Second Embodiment

Figure 8:
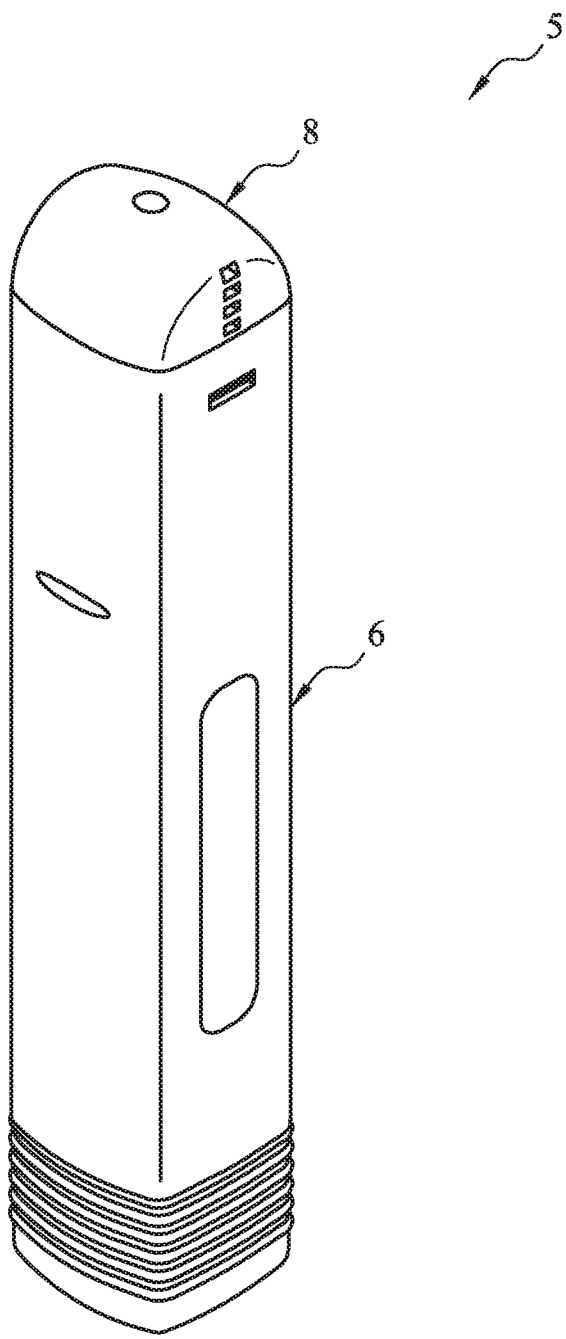
FIG. 8 is an assembled perspective view of the second embodiment of the medicament delivery apparatus according to the present invention.
Figure 9:
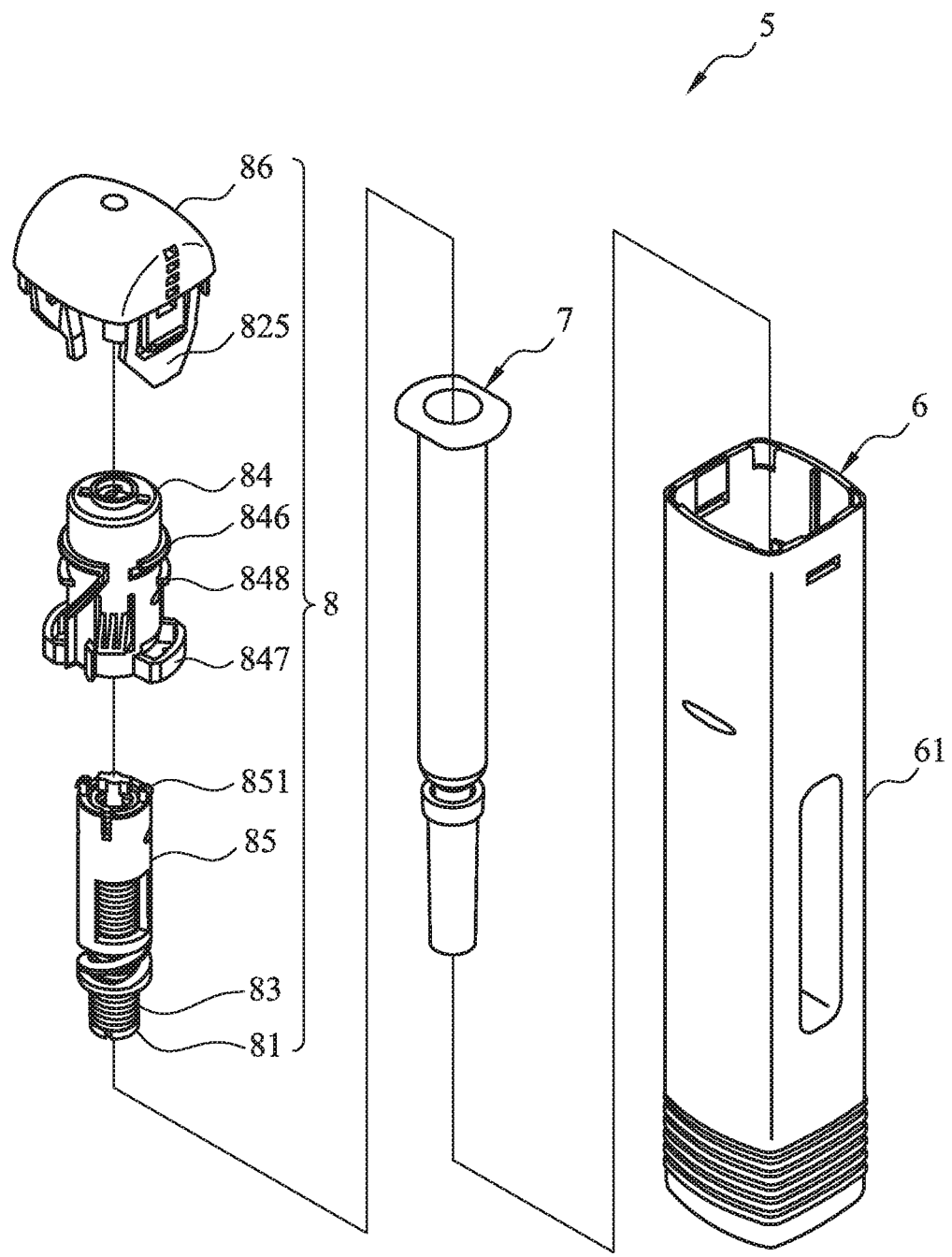
FIG. 9 is an exploded perspective view of the second embodiment illustrating three sub-assemblies.
Figure 10:
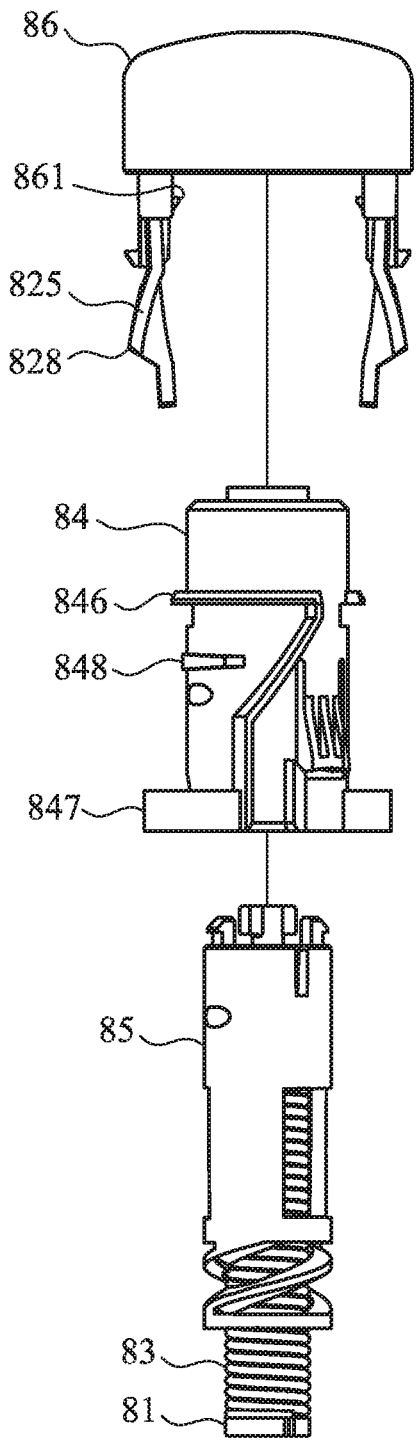
FIG. 10 is an exploded plain view of the first sub-assembly of the second embodiment.
Figure 11A:
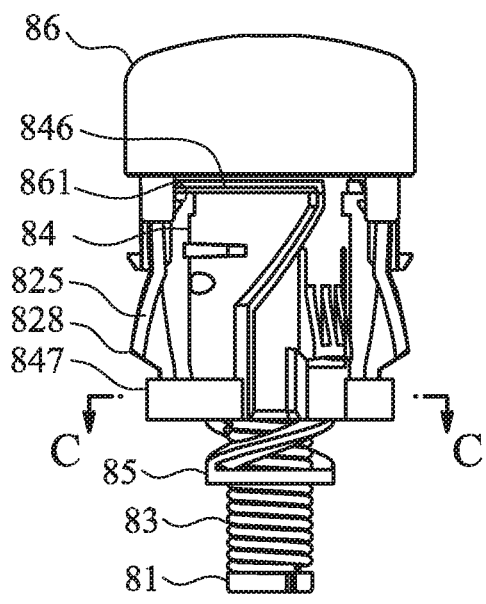
FIG. 11A is an assembled plain view of the first sub-assembly of the second embodiment illustrating a state that a coupling member is locked by a tab.
Figure 11B:
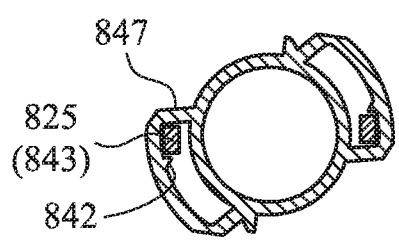
FIG. 11B is a sectional view of FIG. 11A taken along a line C-C.
Figure 12:
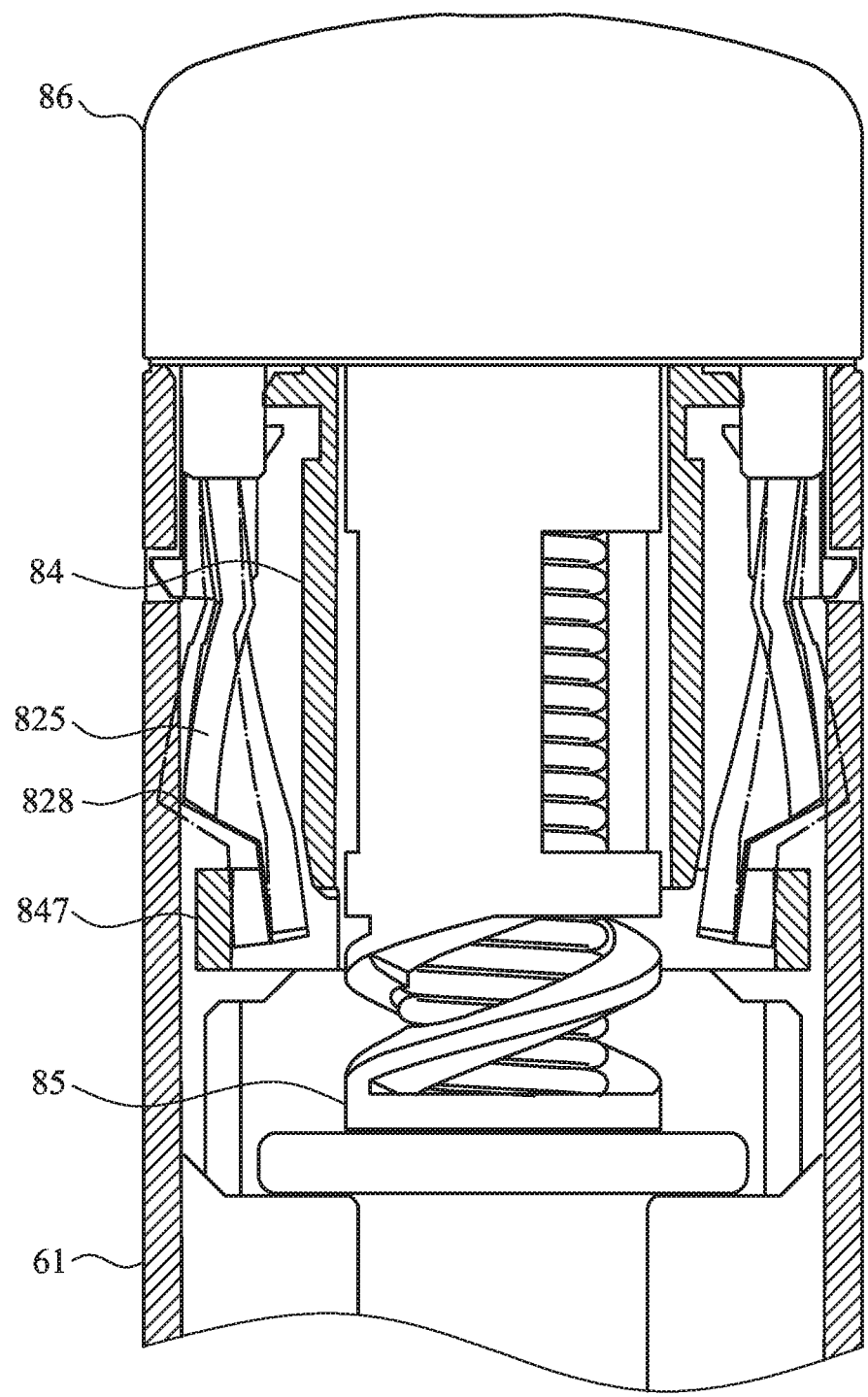
FIG. 12 is a partially enlarged sectional view illustrating different position of a tab in a final assembly of the second embodiment.

As shown in FIGS. 8 and 9, a medicament delivery device 5 with locking elements of the second embodiment has a square or rectangular cross-section, seen in the longitudinal direction. The medicament delivery device 5 comprises a second sub-assembly 6, an intermediate sub-assembly 7 and a first sub-assembly 8. The structure of some elements in the second embodiment may be different from those in the first embodiment. However, the function of the elements may be similar or even identical. Hence, the description of the second embodiment will focus on the first sub-assembly 8 and the connection between the first sub-assembly 8 and the second sub-assembly 6.

The first sub-assembly 8 of the second embodiment comprises a plunger rod 81, a biasing member 83, a biasing member guide 85, a distal cap 86 and a coupling member 84. The biasing member guide 85 has a hook 851 at a distal end thereof for passing through and being fixed to a distal end of the coupling member 84. The biasing member 83 is accommodated within the biasing member guide 85 for biasing the plunger rod 81. The plunger rod 81 is rotatably connected to the distal end of the coupling member 84.

As shown in FIGS. 9~11B, the coupling member 84 includes at least one multi-sectioned ledge 846 on an outer circumferential surface of the coupling member 84, at least one closed loop 847 extending generally radially outwards from a proximal end of the of outer circumferential surface of the coupling member 84, and at least one cam 848 axially located between the ledge 846 and the closed loop 847, which cam extends radially outwards along the outer circumferential surface of the coupling member 84. In the second embodiment, the coupling member 84 may comprise two ledges 846, two closed loops 847 and two cams 848. The cam 848 is ramp-shaped, such that the height of the cam relative to the surface of the coupling member 84 increases along the length of the cam 848. The closed loop 847 has a protrusion 842 which is constituted by the first ramp-shaped surface 844 extending from the inner surface of the closed loop 847 and the second wall-shaped surface 845 extending generally radially and orthogonally from the inner surface of the closed loop 847. The protrusion 842 and a wall profile of the closed loop 847 define a recess 843.

The distal cap 86 includes at least one longitudinal tab 825. In the second embodiment, the distal cap 86 may include two tabs 825 which are oppositely arranged relative to the central longitudinal axis. A latch 861 extends radially inwards at a distal half of the tab 825. A proximal half of the tab 825 may extend outwards and then inwards to form an arch 828. Hence, a distance between the arch 828 of the proximal half and the central axis is larger than the distance between other portions of the tab 825 and the central axis, and also larger than an outer radius of the coupling member 84 and an inner radius of the proximal housing 61.

When the coupling member 84 is assembled with the distal cap 86, the coupling member 84 is substantially received between two tabs 825 and is rotatably connected to the distal cap 86 by means of the latch 861 abutting against a proximal surface of the ledge 846 of the coupling member 84. Furthermore, the free end of the tab 825 is received within the recess 843 and is thus confined. In this state, the coupling member 84 will be prevented from rotation relative to the biasing member guide 85 and distal cap 86. In the second embodiment, the tab 825 is the first locking element and the recess 843 is the second locking element. Engagement of the first locking element with the second locking element rotationally locks the coupling member 84 to the distal cap 86. Hence, the plunger rod 81, which is biased by the biasing member 83, cannot be released from the biasing member guide 85 at an inappropriate occasion, such as during transportation and shipment of the first sub-assembly 8.

As shown in FIGS. 11A~13, when the second sub-assembly 6 and the first sub-assembly 8 are assembled, the distal cap 86 abuts against the inner surface of the proximal housing 61 for a tight fit. During this assembly step, an inner surface of the proximal housing 61 bends the distal half of the tab 825 inwards to the extent that the free end of the tab 825 is completely disengaged and released from the confinement of the protrusion 842 so that the coupling member 84 is ready to be rotated when the medicament delivery device operated by a user.

Figure 15:
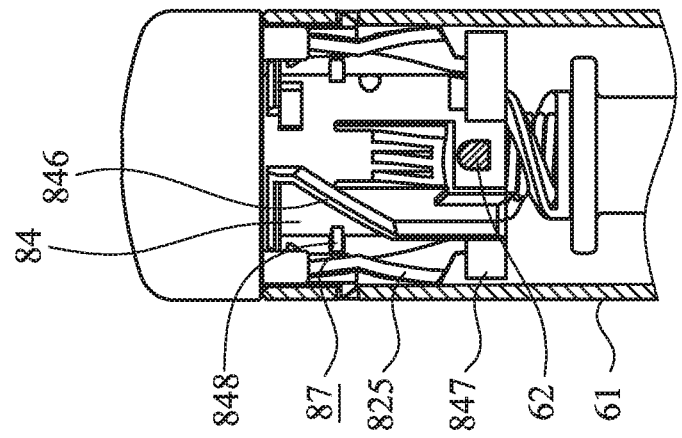
FIG. 15 is view similar to FIG. 14 but the position a protrusion is different from that of FIG. 14.
Figure 14:
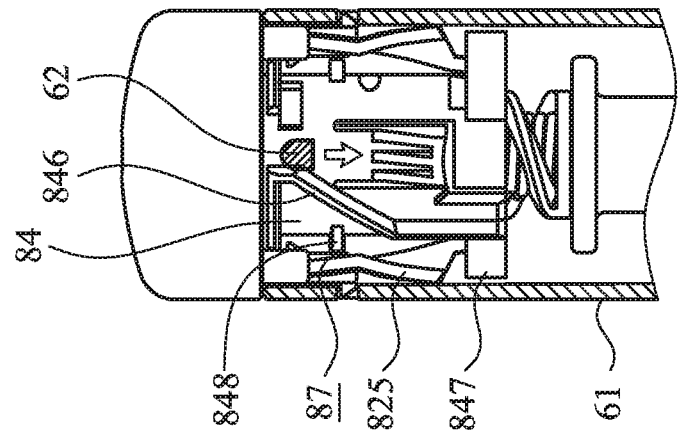
FIG. 14 is view similar to FIG. 13 but the gap disappears.
Figure 13:
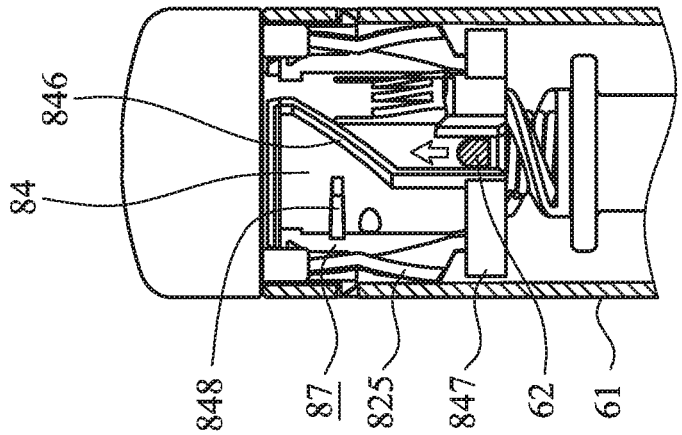
FIG. 13 is a partially enlarged sectional view illustrating a state that a gap exists between a tab and a cam in a final assembly of the second embodiment.

As shown in FIG. 13, when the medicament delivery device 5 is completely assembled and in an initial state, the protrusion 62 of the second sub-assembly 6 is situated on the cylindrical outer surface of the coupling member 84 near the proximal end. In the initial state, there exists a gap 87 between the distal half of the tab 825 and the cam 848 of the coupling member 84. As shown in FIG. 14, when the second sub-assembly 6 is activated, the protrusion 62 of the second sub-assembly 6 slides along the ledge 846 to rotate the coupling member 84 relative to the distal cap 86. In the activated state, the distal half of the tab 825 abuts against the cam 848 because the cam 848 is ramp-shaped around the periphery of the coupling member 84. The rotation of the coupling member 84 closes the gap 87 and the cam 848 supports the distal half of the tab 825 so that it does not deform inwards. As shown in FIG. 15, when an injection is finished, the protrusion 62 of the second sub-assembly 6 longitudinally slides toward the proximal end of the coupling member 84. The cam 848 maintains the abutment against the tab 825 because the coupling member 84 is not rotated during this step.

The features of the distal cap 86 and of the biasing member guide 85 of the second embodiment generally correspond to, or have similar functions as compared to the main body 82 and the plunger rod 81 of the first embodiment.

Third Embodiment

Figure 16:
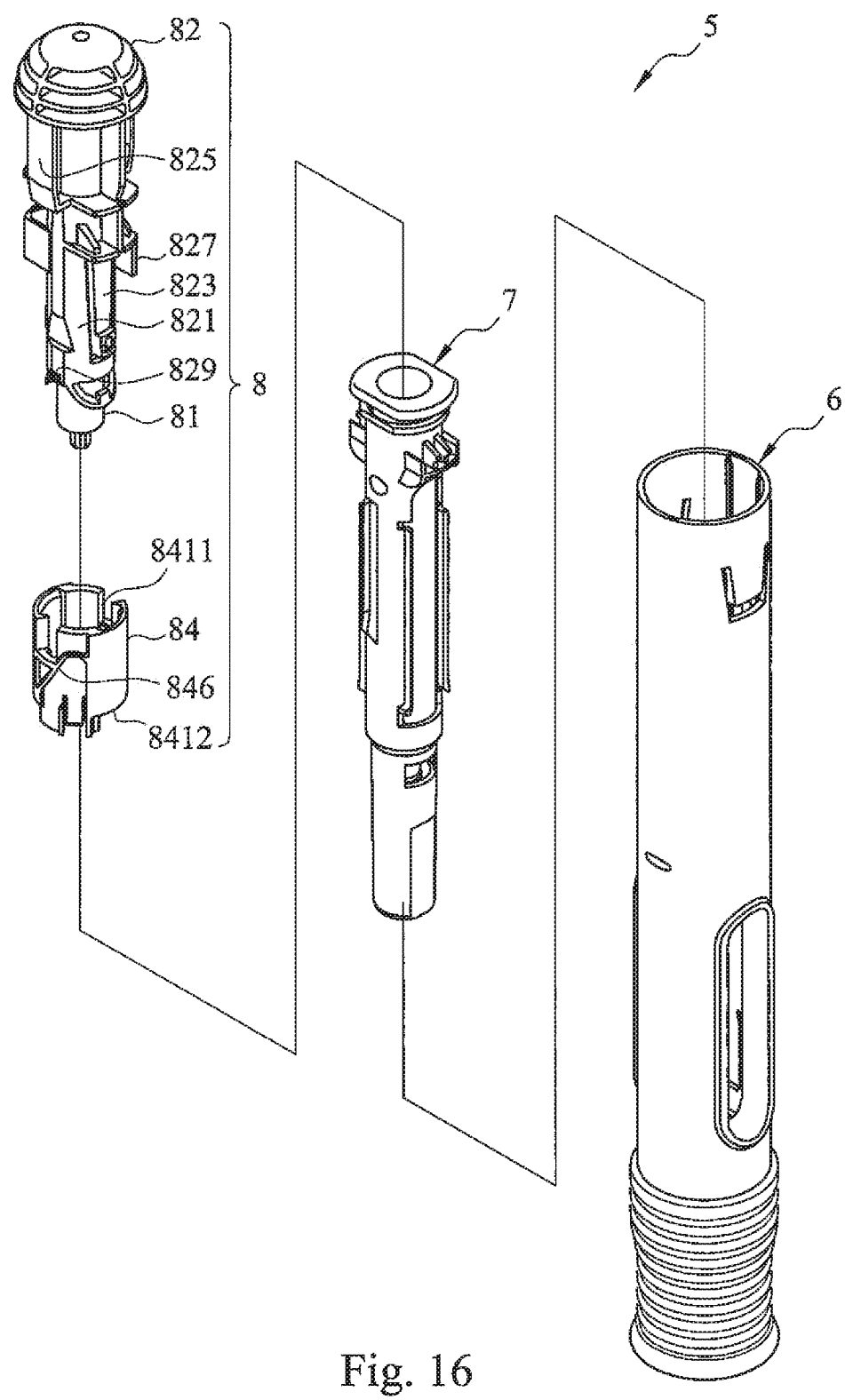
FIG. 16 is an exploded perspective view of the third embodiment of the medicament delivery apparatus according to the present invention illustrating three sub-assemblies.
Figure 17:
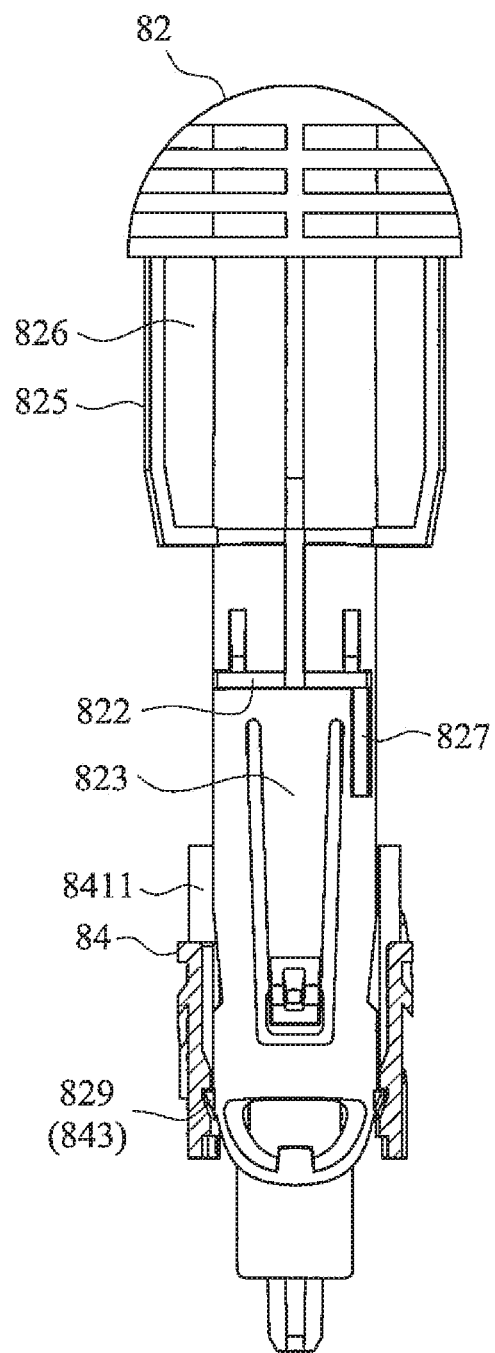
FIG. 17 is a plain and partially sectional view of the first sub-assembly of the third embodiment.

As shown in FIGS. 16 and 17, the main body 82 of the third embodiment comprises a hollow cylinder 821, and a rib 822 which extends radially from the cylinder 821 and divides the cylinder 821 into a proximal section and a distal section. A projection 829 radially extends from a proximal end of the proximal section. At least one tab 825 longitudinally extends from the distal section. In the third embodiment, the main body has two tabs 825 which are oppositely arranged relative to the central axis. A wall 826 radially extends from the cylinder 821 and connects with the tab 825. A shoulder 827 extends proximally from the rib 822. A radially flexible arm 823 is formed in the proximal section. The shoulder 827 and the radially flexible arm 823 are not longitudinally aligned with each other in the axial direction of the main body 82.

The coupling member 84 of the third embodiment comprises a central through-hole through the coupling member 84, a curved ledge 846 on an outer surface of the coupling member 84, a recess 843 formed on an inner surface of the coupling member 84, a first notch 8411 formed at a distal end of the coupling member 84, and a second notch 8412 formed at a proximal end of the coupling member 84. The first notch 8411 and the second notch 8412 are not aligned with each other in the axial direction of the coupling member 84.

When the coupling member 84 is mounted on the proximal section of the main body 82, the projection 829 of the main body 82 is snapped into the recess 843 of the coupling member 84. In the third embodiment, the projection 829 is the first locking element and the recess 843 is the second locking element. Engagement of the first locking element with the second locking element rotationally and axially locks the coupling member 84 to the main body 82. In this state, the distal end of the coupling member 84 does not contact the shoulder 827. Furthermore, the free end of the arm 823 is radially locked by an inner surface of the coupling member 84. Since the coupling member 84 is temporarily locked to the main body 82, the plunger rod 81 which is biased by the biasing member cannot be released from the main body 82 at an inappropriate occasion, such as during transportation and shipment of the first sub-assembly 8.

Figure 18:
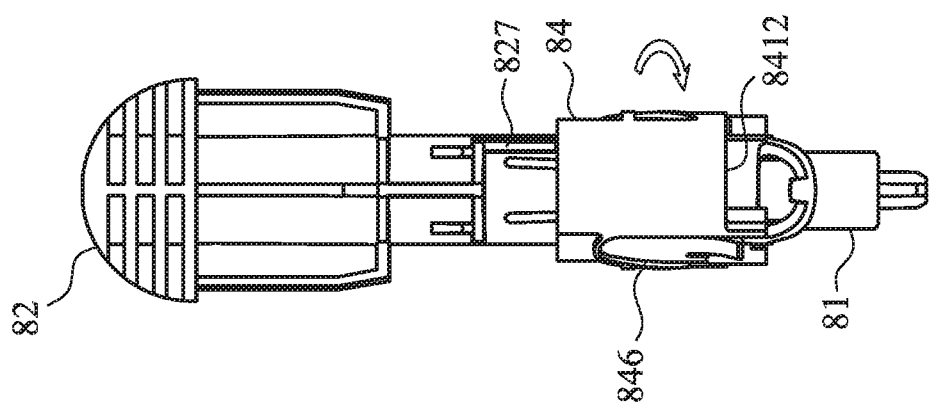
FIG. 18 is a plain view of the first sub-assembly of the third embodiment illustrating a state that the first notch is not aligned with the shoulder.

After the transportation and shipment, the three sub-assemblies 6, 7 and 8 may be assembled to form a final assembly of the medicament delivery device 5. An inner surface of the proximal housing 61 disengages the projection 829 to the extent that the projection 829 is totally released from the recess 843 In the final assembly, the coupling member 84 is slid, by the second sub-assembly 6, along the cylinder 821 of the main body 82 so that the distal end of the coupling member 84 contacts the shoulder 827 of the main body 82 (FIG. 18).

Figure 19:
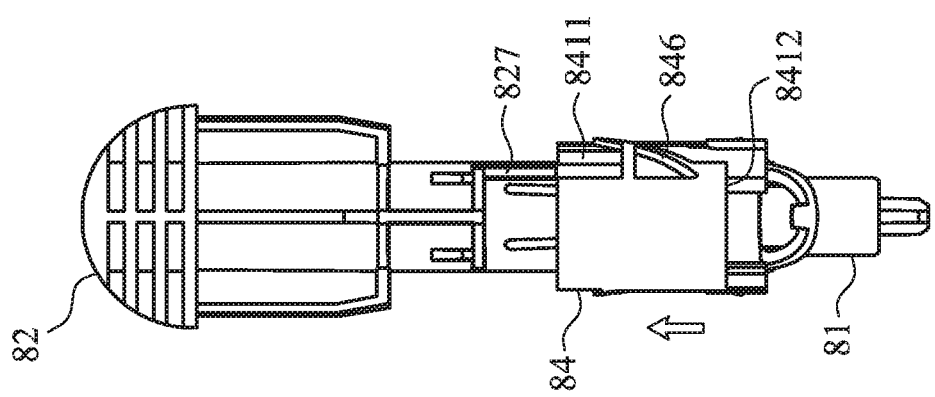
FIG. 19 is a view similar to FIG. 18 but the first notch is aligned with the shoulder.
Figure 20:
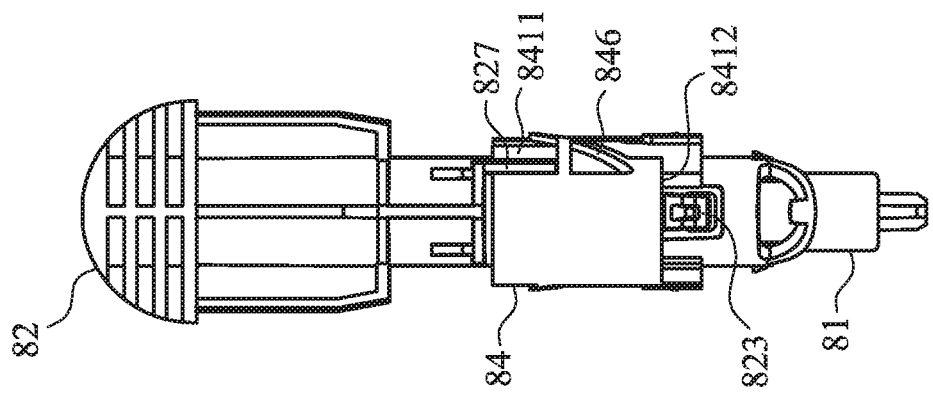
FIG. 20 is a view similar to FIG. 19 but the shoulder is received in the first notch.

As shown in FIGS. 16 and 19, when the second sub-assembly 6 in the final assembly is activated, the protrusion 62 slides along the ledge 846 to rotate the coupling member 84 to the extent that the first notch 8411 of the coupling member 84 is aligned with the shoulder 827 of the main body 82 and the second notch 8412 is aligned with the arm 823. Subsequently as shown in FIGS. 16 and 20, the protrusion 62 of the second sub-assembly 6 further pushes the ledge 846 to move the coupling member 84 axially sliding along the main body 82 and make the shoulder 827 be received within the first notch 8411. At opposite end of the coupling member 84, the free end of the arm 823 of the main body 82 is simultaneously revealed in the second notch 8412. Since, the free end of the arm 823 is no longer locked by the coupling member 84, the arm 823 can spring outwards to release the plunger rod 81 and thus expel medicament in the container 71.

Although three embodiments have been described above with three sub-assemblies, the medicament delivery device 5 may be alternatively performed with two sub-assemblies. Specifically, the intermediate sub-assembly 7 may be incorporated with the second sub-assembly so that the medicament delivery device 5 merely comprises two sub-assemblies (i.e. a second sub-assembly and a first sub-assembly).

The present invention has been disclosed in terms of specific embodiments. It will be apparent that many modifications can be made to the disclosed structures without departing from the present invention. Therefore, it is the intent of the appended claims to cover all such variations and modifications that are within the scope of the present invention.

What is claimed is:

1. A sub-assembly of a medicament delivery device, the sub-assembly comprising:
   a plunger rod comprising an outer surface, where the plunger rod is biased;
   a main body extending longitudinally to partially surround the outer surface of the plunger rod, where the main body comprises a flexible arm that is directly and releasably connected to the outer surface of the biased plunger rod; and
   a coupling member axially fixed, partially surrounding, and rotatable relative to an outside surface of the main body such that the outside surface of the main body is between the outer surface of the plunger rod and an inner surface of the coupling member when the coupling member rotates from a first position to a second position, where the inner surface of the coupling member confines the flexible arm in a locking engagement with the outer surface of the plunger rod to prevent axial movement of the plunger rod when the coupling member is in the first position,
   wherein the main body comprises a first locking element and the coupling member comprises a second locking element having a protrusion extending radially inward from an inner surface of the coupling member,
   wherein rotation of the coupling member from the first position causes the first locking element and the second locking element to be releasably engaged with each other such that the coupling member is prevented from rotating to an axial release position relative to the main body, and
   wherein movement of the coupling member to the second position allows the flexible arm to disengage from and unlock the plunger rod,
   wherein the first locking element extends in an axial direction from the main body, then extends radially outwards in an arch, and then extends radially inwards so that a free end of the first locking element is engaged with the second locking element to prevent the coupling member from rotating relative to the main body.

2. The sub-assembly of the medicament delivery device according to claim 1, wherein a distance between the arch and a central axis of the main body is larger than a distance between the central axis and other portions of the first locking element, and also larger than an outer radius of the coupling member.

3. The sub-assembly of the medicament delivery device according to claim 2, wherein the coupling member includes a bore at a distal end thereof and where the protrusion delimits the second locking element.

4. The sub-assembly of the medicament delivery device according to claim 3, wherein the protrusion has a ramp-shaped first surface which extends inwards from an inner surface of the bore for bending the first locking element and a wall-shaped second surface which extends orthogonally from the inner surface of the bore, for fixing the first locking element relative to the coupling member.

5. The sub-assembly of the medicament delivery device according to claim 4, wherein the main body further includes a biasing member guide which is fixed to the coupling member and a distal cap in relation to which the coupling member is rotatable.

6. The sub-assembly of the medicament delivery device according to the claim 5, wherein the first locking element extends from the distal cap, the distal cap comprises a latch at a distal half thereof, the coupling member comprises a ledge, and the latch is engaged with the ledge to prevent the coupling member from releasing out of the distal cap in the axial direction.

7. The sub-assembly of the medicament delivery device according to claim 3, wherein the first locking element is a radially flexible tab and the second locking element is a recess.

8. The sub-assembly of the medicament delivery device according to the claim 3 wherein the sub-assembly further comprises a biasing member which biases the plunger rod.

9. The sub-assembly of the medicament delivery device according to claim 2, wherein the main body includes a rib which divides the main body into a proximal section and a distal section, and wherein the coupling member is arranged on the proximal section, and a fixed end of the first locking element is arranged on the distal section.

10. The sub-assembly of the medicament delivery device according to claim 2, wherein the coupling member comprises a closed loop at an outer proximal end thereof, and the protrusion situated in the closed loop, and wherein the protrusion and a profile of the closed loop delimit the second locking element for preventing the coupling member from rotating relative to the main body.

11. The sub-assembly of the medicament delivery device according to claim 1, wherein the first locking element radially extends at a free end of the main body, the second locking element is arranged on the inner surface of the coupling member, and the first locking element is engaged with the second locking element to prevent the coupling member from rotation and axial movement relative to the main body.

12. The sub-assembly of the medicament delivery device according to claim 11, wherein the main body comprises a rib which divides the main body into a proximal section and a distal section, the coupling member is arranged on the proximal section.

13. The sub-assembly of the medicament delivery device according to the claim 11, wherein the first locking element is a projection and the second locking element is a recess.

14. A sub-assembly of a medicament delivery device, the sub-assembly comprising:
   a plunger rod which is biased;
   a main body comprising a flexible arm that is directly and releasably connected to the biased plunger rod; and
   a coupling member rotatable relative to the main body and the plunger rod from a first position to a second position and is axially fixed relative to the main body, where the coupling member confines the flexible arm in a locking engagement with the plunger rod to prevent axial movement of the plunger rod when the coupling member is in the first position,
   wherein the main body comprises a first locking element and the coupling member comprises a second locking element having a protrusion extending radially inward from an inner surface of the coupling member,
   wherein rotation of the coupling member from the first position causes the first locking element and the second locking element to be releasably engaged with each other such that the coupling member is prevented from rotating to an axial release position relative to the main body,
   wherein movement of the coupling member to the second position allows the flexible arm to disengage from and unlock the plunger rod, and
   wherein the first locking element extends in an axial direction from the main body, then extends radially outwards in an arch, and then extends radially inwards so that a free end of the first locking element is engaged with the second locking element to prevent the coupling member from rotating relative to the main body.

* * * * *